Aug. 20, 1935. T. J. WOLFE Plant Pat. 135
ROSE
Filed March 22, 1935
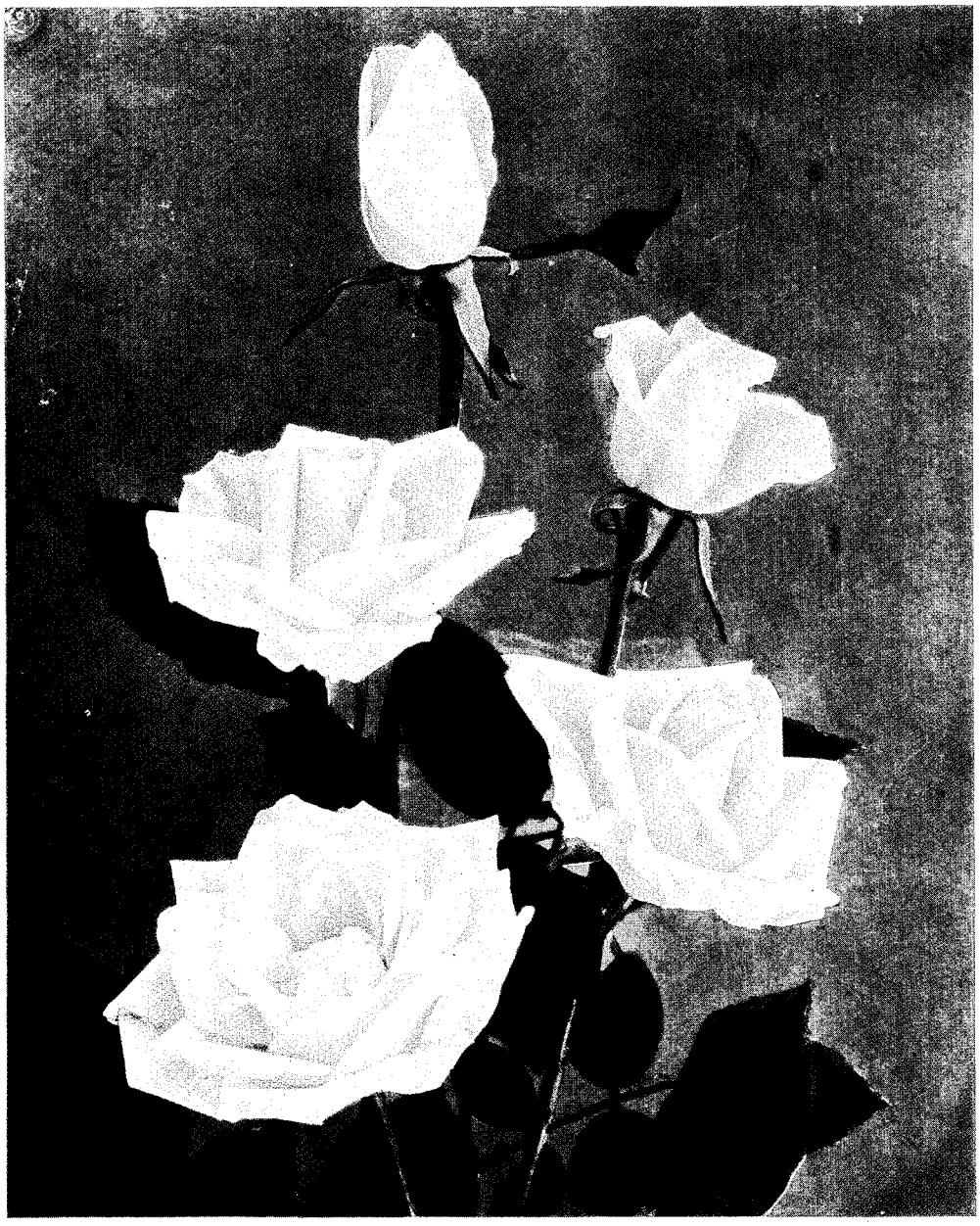
Inventor
Thomas James Wolfe
By Robb & Robb
Attorneys Patented Aug. 20, 1935

UNITED STATES PATENT OFFICE

135

ROSE

Thomas James Wolfe, Waco, Tex.

Application March 22, 1935, Serial No. 12,513

1 Claim. (Cl. 47—61)

The present discovery relates to a new and distinct variety of rose plant originating as a sport from the well known variety "President Herbert Hoover".

In its development I have found this new rose distinct from its parent and from other similar varieties in several important respects, namely endurance and ability to stand punishment and abuse in shipment over long distances as a cut flower enabling it to come back quickly; attractive color of its flower and foliage; and the length of its stems from natural growth, making it a cutting rose of great excellence. In addition to these characteristics, this new variety is notable for its heavy and prolific growth, by virtue of which it stands as an extremely desirable garden rose.

With reference to its cut flower characteristics which go to make it an unusually desirable variety, tests have been made showing that flowers may be cut in a very tight bud stage, often when color may not yet be seen, and still the flowers will develop perfectly in water and last for weeks. Furthermore, buds and flowers cut one afternoon and shipped for several hundred miles without putting in water and with just ordinary wrapping and packing to carry the same, have reached their destinations 36 to 40 hours later and the flowers have opened and lasted a week or better.

In regard to its growth I find that often stems from 20" to 30" long occur as natural growth, eliminating the necessity of pinching to obtain stem length.

Asexual reproduction has shown these marked characteristics to be permanent or fixed.

The following is a detail description of this new rose plant:

Parentage:

Sport of variety "President Herbert Hoover".

Classification:

Botanic—Hybrid tea.

Under which it will be introduced in commerce "Hybrid tea".

*Flower*

Blooming habit:

Blooms profusely.

Recurrent: Continuous.

Other habit: Very free flowerer.

Bud:

*Size.*—Very large.

*Form.*—Very long. Unaffected by wet or hot weather.

*Color.*—When sepals first divide—canary; when petals begin to unfurl—gold. When half blown outside row inside petal light aurora. Outside row outside petal gold. Inner petals inside straw to gold. Inner petals outside gold. (Name of color standard used Gravereaux system).

*Sepals.*—Smooth edge; hood above bud; curl back when half open.

*Calyx.* — Shape — funnel. Size — large, long. Aspect—hairy and glandular to mossy to slight degree. Odor when rubbed like tea but little more acrid.

*Peduncle.*—Length medium. Aspect prickly. Color medium green. Strength erect. Opening—Bud opens well. Unaffected by adverse conditions.

Bloom:

*Size.*—Very large. Average size when fully opened six inches and over.

*Borne.*—Singly.

*Stems.*—Long, strong.

*Form.*—When first open slightly cupped. Permanence—outer petals curl back and flatten slightly.

*Petalage.*—Double (full but open center.) Number of petals under normal conditions 26 to 32.

*Color.*—(Gravereaux system.) Center of flower gold. Outer petals light aurora. Base of petals (aiglet) light saffron. Inside of petals straw to gold. Reverse of petals gold to light saffron. General tonality from a distance gold with pink tint.

*Variegations.*—Veined slightly.

*Discoloration.*—General tonality:—Second day same as first day only pink tint very light. Third day lightens in color slightly. More gold with pink tint diminishing.

Petals:

*Texture.*—Soft. Unaffected by hot or wet weather.

*Appearance.*—Inside velvety; outside satiny.

*Form.*—Round; to broad oval.

*Arrangement.*—Imbricated (regularly arranged shingle like). Petaloids in center; small.

*Persistence.*—Hang on and dry.

*Fragrance.*—Strong. Nature "Old Rose Perfume" (Centifolia).

*Lasting quality.*—On the plant and as a cut flower very long.

Genital organs:

*Stamens, anthers.*—Medium, many. Color—reddish brown. Arrangement—tucked in calyx or partly so.

*Stamens, filaments (threads).*—Medium. Color—yellow.

*Pollen.*—Gold yellow.

*Styles.*—Bunched, uneven length. Medium length heavy.

*Stigmas.*—Color red to purple.

*Ovaries.*—All enclosed in calyx.

*Plant*

Form:

Bush.

Growth:

Very vigorous, upright.

Foliage:

Leaflets 5 to 7.

*Size.*—Large.

*Quantity.*—Normal.

*Color.*—New foliage—upper side light green to dark green; under side bronzy. Old foliage—upper side dark green; under side light green.

*Shape.*—Oval pointed.

*Texture.*—Upper side glossy; under side velvety; ribs and veins ordinary.

*Edge.*—Serrated.

*Serration.*—Double to single, small, sharp.

*Leaf stem.*—Reddish color; under side prickles.

*Stipules.*—Medium, smooth.

*Disease resistance.*—Resistant.

Wood:

*New wood.*—Color reddish, bronzy; bark smooth.

*Old wood.*—Color green, brown, streaky; bark smooth to rough.

Thorns:

*Thorns.*—Quantity—on main stalks from base many; on laterals from stalk many. Form—narrow base; long to medium; hooked downward. Color when young—green and red. Position—irregular.

*Prickles.*—Quantity—on main stalks few to none; on laterals—few to none. Color—green to brown.

*Short needles.*—Quantity—on main stalks few to none. On laterals few to none.

I claim:

A new and distinct variety of rose plant substantially as shown and described, characterized by its long stem, heavy and prolific growth, the endurance and ability as a cut flower to stand punishment and abuse in shipment, and the novel color of its flower and foliage.

THOMAS JAMES WOLFE.